(12) United States Patent
Band et al.

(10) Patent No.: US 10,188,303 B2
(45) Date of Patent: Jan. 29, 2019

(54) HEMODYNAMIC MONITOR AND METHOD OF HEMODYNAMIC MONITORING

(75) Inventors: David Marston Band, Worplesdon (GB); Terence Kevin O'Brien, Cambridge (GB); Eric Mills, London (GB); Christopher Bancroft Wolff, Cambridge (GB); James Arthur Douglas, Kings Langley (GB)

(73) Assignee: LIDCO Group PLC, London (GB)

(*) Notice: Subject to any disclaimer, the term of this patent is extended or adjusted under 35 U.S.C. 154(b) by 964 days.

(21) Appl. No.: 13/578,334

(22) PCT Filed: Feb. 10, 2011

(86) PCT No.: PCT/GB2011/000176
§ 371 (c)(1),
(2), (4) Date: Sep. 14, 2012

(87) PCT Pub. No.: WO2011/098763
PCT Pub. Date: Aug. 18, 2011

(65) Prior Publication Data
US 2013/0006126 A1    Jan. 3, 2013

(30) Foreign Application Priority Data
Feb. 11, 2010 (GB) .................................. 1002331.5

(51) Int. Cl.
A61B 5/029 (2006.01)
A61B 5/02 (2006.01)
A61B 5/021 (2006.01)

(52) U.S. Cl.
CPC .............. *A61B 5/029* (2013.01); *A61B 5/021* (2013.01); *A61B 5/02028* (2013.01); *A61B 5/02108* (2013.01)

(58) Field of Classification Search
CPC ...... A61B 5/029; A61B 5/02028; A61B 5/021
See application file for complete search history.

(56) References Cited

U.S. PATENT DOCUMENTS 3,835,839 A * 9/1974 Brown .................... A61B 5/026
600/506
4,834,107 A    5/1989 Warner
(Continued)

FOREIGN PATENT DOCUMENTS

EP    1045718 B1    5/2004
EP    2533685       12/2012
(Continued)

OTHER PUBLICATIONS

International Search Report corresponding to co-pending International Patent Application Serial No. PCT/GB2011/000176, European Patent Office, dated Apr. 20, 2011; (4 pages).
(Continued)

*Primary Examiner* — Jacqueline Cheng
*Assistant Examiner* — Tho Tran
(74) *Attorney, Agent, or Firm* — Nixon Peabody LLP

(57) ABSTRACT

An apparatus and method for determining stroke volume. The apparatus receives an arterial pressure waveform and is arranged to correct a part of the pressure waveform that relates to a heart beat for an influence of an ectopic heart beat, of atrial fibrillation on the pressure waveform or of changes in the pressure waveform's baseline. The apparatus also comprising means arranged to calculate the stroke volume from the corrected waveform.

12 Claims, 6 Drawing Sheets

(56) References Cited

U.S. PATENT DOCUMENTS

| | | | |
|---|---|---|---|
| 5,743,267 A * | 4/1998 | Nikolic | A61B 5/0028 128/903 |
| 2001/0056242 A1* | 12/2001 | Palti | A61B 5/022 600/490 |
| 2005/0154422 A1* | 7/2005 | Band | A61N 1/3627 607/17 |
| 2006/0167361 A1 | 7/2006 | Bennett et al. | |
| 2006/0235323 A1 | 10/2006 | Hatib | |
| 2008/0183232 A1* | 7/2008 | Voss | A61B 5/02028 607/24 |
| 2009/0131805 A1 | 5/2009 | O'Brien et al. | |
| 2010/0076326 A1 | 3/2010 | Cohen | |
| 2010/0152592 A1* | 6/2010 | Hatib | A61B 5/021 600/485 |
| 2013/0006126 A1 | 1/2013 | Band et al. | |

FOREIGN PATENT DOCUMENTS

| | | |
|---|---|---|
| JP | S4731655 A | 11/1972 |
| JP | S6111020 A | 1/1986 |
| JP | H0532085 Y2 | 8/1993 |
| WO | WO 93/09427 | 5/1993 |
| WO | WO 97/00017 | 1/1997 |
| WO | WO 97/24982 | 7/1997 |
| WO | WO 00/64339 | 11/2000 |
| WO | WO 2008/144404 A1 | 11/2008 |
| WO | 2009/068233 A2 | 6/2009 |

OTHER PUBLICATIONS

International Written Opinion corresponding to co-pending International Patent Application Serial No. PCT/GB2011/000176, European Patent Office, dated Apr. 20, 2011; (7 pages).

European Office Action corresponding to co-pending European Patent Application Serial No. 11705649.9, European Patent Office, dated Jul. 29, 2015; (4 pages).

Rhodes et al., "Arterial Pulse Power Analysis: The LiDCO™plus System", Functional Hemodynamic Monitoring Update in Intensive Care and Emergency Medicine, 42, pp. 183-192, 2005.

Wolff et al., "A Simple Volume Related Model of Arterial Blood Pressure Generation", Adv. Exp. Med. Biol., vol. 614, pp. 109-117, 2008.

Liu et al., "Aortic Compliance in Human Hypertension", Hypertension, 1989, 14: pp. 129-136.

Lysander et al., "Non-Invasive Pulsatile Arterial Pressure from the Human Finger", Experimental Physiology, 90:4, pp. 437-446, 2005.

Jonas et al., "Real Time, Continuous Monitoring of Cardiac Output and Oxygen Delivery", in International Journal of Intensive Care, vol. 9, No. 1, pp. 33-42, 2002.

International Search Report for Application No. GB1002331.5, Intellectual Property Office UK, dated Jun. 30, 2010, 2 pages.

international Examination Report for Application No. GB1002331.5, Intellectual Property Office UK, dated Jul. 1, 2010, 5 pages.

Notice of Reasons for Rejection for Japanese Patent Application No. JP 2012-552460, dated Oct. 15, 2014, 2 pages.

\* cited by examiner

HEMODYNAMIC MONITOR AND METHOD OF HEMODYNAMIC MONITORING

CROSS-REFERENCE TO RELATED APPLICATIONS

This application is a U.S. National Stage of International Application No. PCT/GB2011/000176, filed Feb. 10, 2011, which claims the benefit of United Kingdom Patent Application No. 1002331.5, filed on Feb. 11, 2010, both of which are incorporated herein by reference in their entireties.

FIELD OF THE INVENTION

The present invention relates to a method and apparatus for determining the left ventricular stroke volume of a heart. In particular the present invention relates to determining stroke volume in arrhythmic or irregular heart beat conditions or in situations where the blood pressure is changing.

BACKGROUND

An accurate knowledge of the hemodynamic status/cardiac output of the heart of a patient helps medical practitioners assess a patient's medical condition. The constituents of cardiac output (measured, for example, in liters/minute), heart rate (measured, for example in beats per minute) and stroke volume (measured for example in mls) may also provide useful information. The stroke volume, or cardiac stroke volume, is the volume of blood ejected by the left ventricle during systole across the aortic valve forwards into the aorta during each cardiac contraction. This volume normally corresponds to the volume of blood in the left ventricle at the end of the systole minus the pre-systole diastolic volume of the left ventricle. This is particularly true in acute situations, such as, for example, for patients in intensive care units or patients undergoing an operation where for example it is used in fluid and drug management during anaesthesia and after. Knowledge of a patient's cardiac output, or its constituents, may, moreover, be beneficial in less critical or less life threatening situations, such as in situations where the monitoring of the patient is generally desirable.

It has long been known that cardiac output as well a stroke volume and heart rate can be determined based on an analysis of arterial blood pressure waveform. Summaries of previously suggested methods for the determination of the output of the heart are provided in WO 97/00017, a prior patent disclosure of the present assignee, and in A. Rhodes, R. Sunderland, "Arterial Pulse Power Analysis: The LiDCO™ plus System", Functional Hemodynamic Monitoring Update in Intensive Care and Emergency Medicine, 42, pp. 183-192, 2005, the entireties of which are incorporated herein by this reference.

WO 97/00017 discloses evaluating an arterial pressure waveform by performing a volume transformation followed by an autocorrelation operation applied between a part of the transformed pressure waveform comprising first and second pressure pulses of a patient's heart. An analysis of this nature requires that data representing a second heart beat be first acquired before the data can be analysed and an indication of the patient's hemodynamic status, including stroke volume, heart rate and/or cardiac output, can be provided. The indication of the patient's hemodynamic status can thus only be provided with a slight delay.

It was realised that in acute scenarios it may be desirable for an indication of cardiac output to track the patient's actual cardiac output in real time so that an indication of cardiac output/hemodynamic status can be provided for each heart beat. Such beat-by-beat tracking requires that stroke volume be determined based on pressure data relating to a single heart beat only. It is therefore desirable for data relating to a single heart beat to be extracted from the arterial pressure waveform.

SUMMARY OF THE INVENTION

According to an aspect of the present invention there is provided an apparatus for determining cardiac stroke volume comprising an input for receiving a temporal arterial pressure waveform, means for defining a start point for further data analysis within the waveform at the beginning of a systolic arterial pressure increase and means arranged to determine a non-arbitrary and defined end point for the further data analysis. The end point is determined by performing at least one or both of identifying a part or point of the waveform that has substantially the same value as said starting point or, if the waveform does not comprise a part or point that has substantially the same value as the starting point, by extrapolating the waveform from the end of the diastole to a point where it has substantially the same value as at the starting point. The end of the diastole may in this context be considered a point at which, after a decrease in pressure values, a renewed pressure increase starts to occur. The apparatus further comprises means for calculating the stroke volume from a part of the waveform or of the extrapolated waveform that extends between the starting point and the end point.

A normal heart beat is composed of two successive periods, systole and diastole. During the systole due to ventricular contraction the pressure inside the left ventricle of the heart increases to a point at which the aortic valve opens and blood is ejected into the aorta. This causes an increase of pressure in the aorta and a consequential elastic expansion of the aorta. The pressure in the aorta increases up to shortly before the closing of the aortic valve. The aortic valve then closes shortly after the pressure inside the heart falls below the aortic pressure. Thereafter aortic pressure decreases (to its lowest value—the diastolic pressure) as the ejected blood flows out of the aorta into the periphery until blood is once again ejected from the heart's ventricle during the next systole. This decrease in aortic pressure during diastole is, however, gradual as it is mediated by an elastic contraction of the aorta against the total peripheral resistance of the systemic circulation. This function of the aorta to act as a buffering chamber to store a proportion of the left ventricular stroke volume during systole may be referred to as the Windkessel function.

It was realised in light of the above that, if cardiac output or stroke volume is assessed using aortic pressure or a pressure measured in a more peripheral artery, such as, for example the basilic, radial, femoral, axillary or pedal artery as a basis, as is the case in the present invention, then the entirety of the aortic pressure waveform, from the beginning of the systolic pressure increase in the arteries to the point where the arterial pressure has decreased to the starting pressure, ought to be considered. It has been realised that there are situations in which the arterial pressure waveform may be distorted by events that are not related to the actual cardiac output/stroke volume of the heart during a particular beat. For example, if an ectopic heart beat or atrial fibrillation creates a more rapid onset left ventricular contraction, then the aortic pressure increase created by this ectopic beat will be overlaid over and therefore interrupt the diastolic descending part of the previous beat's arterial pressure waveform. The fact that part of the previous beat's pressure waveform has been distorted or cut short by such an additional or early beat does of course not mean that contribution of the elastic expansion of the aorta created by the earlier beat has become irrelevant or can be ignored for the purposes of calculating cardiac output and stroke volume. On the contrary, the aorta still has elastically stored/retained (as potential energy) part of the energy provided during the elastic expansion during the systolic pressure increase created by the ejection phase of the earlier heart beat. It was realised that, for the volume of the earlier beat/stroke to be adequately evaluated, it is desirable that the entire diastolic part of the arterial pressure waveform be available for evaluation in a form it would have had, had it not been for the interference created by the additional/earlier ectopic heartbeat.

Thoracic pressure may also influence the appearance of the arterial pressure waveform. The movement of the diaphragm and the ribcage, for example, causes thoracic pressure to dynamically change between the negative and positive pressure values (when compared to atmospheric pressure) that are required for inhalation and exhalation respectively. Similar continuous or dynamic changes in thoracic pressure are also present in a patient on a ventilator, although thoracic pressure changes are between different positive pressure values (again when compared to the surrounding atmospheric pressure) in this case.

It will be appreciated that such fluctuations in thoracic pressure can change the pressure surrounding the central veins, pulmonary artery and the aorta over the course of a single heart beat. This can manifest itself in the form of baseline fluctuations in measured arterial pressure waveforms. When a patient exhales naturally, for example, the associated increase in thoracic pressure may cause the diastolic pressure, that is the pressure to which the arteries relax after the end of the systole, to be higher than the corresponding diastolic pressure at the end of the preceding heart beat, which is the beginning of a current heart beat. The expulsion of blood from the ventricle, however, will have been completed at a pressure different from the pressure experienced by the aorta at the end of diastole. Based on this it was realised that, for the volume of the beat/stroke to be adequately evaluated, it is desirable that the diastolic part of the arterial pressure waveform be evaluated in a form it would have had in the absence of the pressure fluctuations created by the patient's exhalation.

It will be appreciated that the above is also true for heart beats occurring while the patient inhales naturally. Thoracic pressure is gradually reduced at the beginning of inhalation and it may thus be that the pressure at the beginning of the systole, that is the pressure against which the heart needs to eject blood and elastically expand the aorta, is higher than the pressure at the end of the diastolic part of the aortic pressure waveform. Based on this it was again realised that, for the volume of the beat/stroke to be adequately evaluated, it is desirable that the diastolic part of the arterial pressure waveform be evaluated in a form it would have had in the absence of the pressure fluctuations created by the patient's respiration.

It was realised that a number of factors, such as the factors discussed above by way of example, influence the appearance of the arterial pressure waveform. While some such influences, such as respiratory changes in thoracic pressure, may not cause undue degradation of a measurement of cardiac output if such a measurement is based on averaging values from a number of heart beats, their effect on a determination of the blood volume ejected by the heart in a single stroke (the stroke volume) may be more noticeable.

Other influences on the appearance of the arterial pressure waveform, such as atrial fibrillation, are known to become more prevalent with increasing age. In atrial fibrillation the normal electrical impulses that are generated by the sinuatrial node may be overwhelmed by disorganized electrical impulses originating in the atria, leading to conduction of irregular impulses to the ventricles and thus generating an irregular ventricular contraction/heartbeat. Such irregular heartbeats are known as atrial fibrillation and may occur in acute episodes lasting from minutes to weeks or months. Atrial fibrillation may also persist over years. Given that the average age of patients has been increasing for some time and is set to continue to increase in the future, it is desirable for an accurate method of determining stroke volume and cardiac output to be devised to work even under such adverse conditions.

The present invention alleviates or overcomes at least some of the above problems by only considering a part of the arterial pressure waveform that relates to one heart beat. For this purpose a starting point for these data considerations is defined as a data point at the beginning of the systolic arterial pressure increase. The data value at this point in time is used as a reference value and a further point is searched for at which the same arterial pressure value again occurs. This further point is defined as the end point of the heart beat for the purpose of data processing and the stroke volume is then determined taking into account the part of the pressure waveform between the starting point and the end point. Any drop in arterial pressure that may be caused by the patient's breathing or ventilation is thus simply ignored. Treating the arterial pressure waveform in this manner was found to reduce the number of occasions where the stroke volume could not be determined or had clearly been determined incorrectly, when compared to a technique in which stroke volume is determined based on an analysis of two heart beats.

As discussed above, a situation can be envisaged where arterial pressure does not fall to the value it had at the start of the heart beat prior to the next heart beat, be that because of respiratory effects, or because of the early onset of the next heart beat. In situations of this nature the end point of the part of the pressure waveform that is to be used for determining the stroke volume of the heart beat is defined as being beyond the "beginning" of the next heart beat. The shape or downslope of the arterial pressure curve up to the beginning of the next/additional beat (which will be characterised by a pressure reduction due to the flow-off of blood to the periphery) is then extrapolated to the time point at which it has a value that corresponds to the value it had at the start of the heart beat. Such extrapolation may take the form of a linearly descending set of values. Using such linear extrapolation has the advantage that minor deviations from a normally linearly descending diastolic pressure waveform can robustly be ignored. It is known that arterial pressure decrease substantially follows an exponential function (e.g. Liu, Z. R., Ting, C. T., Zhu, S. X., Yin, F. C., "Aortic compliance in human hypertension", Hypertension, 1989, 14:129-136). Computationally inexpensive linear extrapolation can provide an adequate approximation of this exponential function in the arterial pressure range of significance in clinical situations. Alternatively an exponential function may be fitted to the available data points of the arterial pressure decrease to extrapolate to the point where the predicted/extrapolated pressure is the same as the pressure at the starting point. The end point of the part of the pressure waveform that is to be used for determining the stroke volume of the heart beat is then defined as the extrapolated point having substantially the value of the waveform at the start of the heart beat. By extrapolating in this manner it is again possible to simply ignore pressure variations due to a patient's respiration. More importantly, however, the extrapolation technique disclosed herein allows one adequately to evaluate those parts of a pressure waveform that may have been distorted or masked by an additional heart beat. The beginning of the next heart beat may be determined and used as a reference point from which to extrapolate the pressure waveform. Methods for determining the beginning of a heart beat are known to the person skilled in the art. One way of determining the starting point of a heartbeat from an arterial pressure waveform could be to detect the point where the gradient of the pressure waveform changes from negative to positive.

Extrapolating the pressure waveform, if necessary, may take the form of determining a trend in the later part of the pressure waveform, for example in the second half, or the last third, quarter or fifth of the waveform between the determined beginning of the beat under consideration and the determined beginning of the next beat, and continuing this trend until a value corresponding to the value at the beginning of the current heart beat is reached. This may, for example, be achieved by determining the gradient in this later part of the waveform and by continuing the waveform by way of extrapolation, using this gradient until a value corresponding to the value at the beginning of the current heart beat is reached. Extrapolation may, however, also be achieved in any other suitable manner. It can, for example be envisaged that a suitable function be fitted to the data of the later part of the arterial pressure waveform and that the pressure waveform is then extrapolated by applying the thus appropriate function beyond the data point until a value corresponding to the value at the beginning of the current heart beat is reached.

The arterial pressure waveform may be derived from a pressure measurement acquired using a catheter in one of the patient's arteries, such as in the radial artery or, for example if already in place, from an aortic catheter. Arterial pressure monitors are commercially available and it is thus not essential that the present apparatus comprises means for measuring the arterial pressure waveform itself, although such means may of course be provided as part of the apparatus of the present invention. More conveniently the arterial pressure waveform may, however, be received from an output of a commercially available invasive arterial pressure monitoring systems, such as the LiDCOrapid or LiDCO™ plus hemodynamic monitors available from LiDCO Ltd. of 16 Orsman Road, London, N1 5QJ, UK. Arterial pressure may alternatively be monitored in a non-invasive manner from the finger using a Finapres and Portapres (Lysander et al., Non invasive pulsatile arterial pressure from the human finger. Experimental Physiology, 90:4, 427-446, 2005).

It will be appreciated that the arterial pressure waveform in isolation from other information does not provide an absolute indication of the amount of blood ejected from the heart with each beat. This is firstly because the increase in pressure is not proportional to the amount of blood ejected from the heart due to the Windkessel function referred to above, paired with the fact that the elastic properties of the arterial compartment are not linear over the diastolic to systolic pressure range. In order to be able to obtain absolute values for the amount of blood ejected from the heart during a heart beat the pressure waveform needs to undergo a non-linear transformation. This can be done, for example, using a look up table comprising information linking pressure increase to the amount of blood ejected from the heart in a beat (the stroke volume). Alternatively a detected change in arterial pressure can be translated into a volume change through the equation disclosed in the above incorporated and referenced paper by A. Rhodes, repeated here for convenience:

$$V = cal \cdot 250(1 - e^{-k \cdot BP}) \quad (1)$$

wherein V is the desired equivalent excess/added volume of the arterial compartment above the starting relaxed/diastolic volume, BP is blood pressure in mmHG, k is a curve coefficient and 250 ml is a typical saturation volume of the arterial system, that is the maximum additional volume that can be added to the arterial system above the filling volume at atmospheric pressure. A curve coefficient k of 0.0092 has been shown to allow to adequately determine the equivalent/excess added volume of the arterial compartment where the blood pressure is measured in mmHg. The calibration factor cal. is provided to adjust the saturation value to individual patients. A further disclosure linking arterial blood volume to arterial blood pressure is provided by C. B. Wolff, B. S. Gooch and J. S. Douglas in "A Simple Volume Related Model of Arterial Blood Pressure Generation", Adv. Exp. Med. Biol., vol 614, pgs 109-117, 2008. The entirety of the disclosure of which is incorporated herein by this reference.

It will be appreciated that the saturation volume may differ between patients and the calibration value cal. of equation (1) thus needs to be determined for each patient if it is desired that an absolute value for the patient's stroke volume be derived. It will, however, be appreciated that, even if the calibration value cal. for a particular patient is unknown, equation (1) can provide a useful beat-by-beat indication of changes in the patient's stroke volume over time. In this case the calibration value cal. may be set to a nominal value of 1.0 (equivalent to a maximal additional volume of 250 ml), so as to enable deriving such relative indications.

The calibration value cal. may be derived using one of a number of calibration techniques, such as, for example, the well known lithium 'dye' calibration technique described by M. Jonas, D. Hett and J. Morgan in "Real Time, Continuous Monitoring of Cardiac Output and Oxygen Delivery", in International Journal of Intensive Care, 2002, Vol. 9, No. 1, the entirety of which is incorporated herein by this reference, using a suitable sensor, such as the sensor disclosed in WO 93/09427. This technique relies on an injection of a bolus of a Lithium Chloride solution into a central vein and records the increase in plasma Lithium ion concentration in a peripheral artery during the first pass of the bolus. The total area of the dilution curve recorded in this way is inversely proportional to the total cardiac output and can be used to derive cal. in a well known fashion. Other similar calibration techniques may also be used. Such techniques include the thermal dilution technique also mentioned in WO 93/09427, other dye dilution techniques, the Fick method and transesophageal ECHO cardiography.

It is moreover possible to estimate the calibration factor based on empirical data relating to patient age and body mass. The calibration factor is known to increase with age and body mass. It will be appreciated that, even if the calibration factor is estimated in this fashion, the calibration factor is still specific to the patient. The above mentioned LiDCOrapid hemodynamic monitor estimates the calibration factor in this fashion.

It will be appreciated that the blood pressure recorded by an arterial pressure sensor depends on a number of factors. The factor that is of interest for the determination of stroke volume is of course the cyclic changes in arterial blood pressure caused by the ejecting of blood from the heart. The flow-off of blood through the arterial system also influences the arterial blood pressure and is determined by the peripheral resistance of the patient. Peripheral resistance will of course vary with time but can be assumed to be constant over the period of a heart beat or a few heart beats. Blood drainage from the arterial system can thus be considered as determining an offset, that is a DC background component of the (AC) dynamic pressure changes caused by the inflow of blood from the heart into the aorta during systole. To determine/distinguish stroke volume i.e. the input blood volume function, it may therefore be desirable to analyse only the pulsatile changes in the arterial pressure curve or the related volume curve.

The method disclosed in WO 97/00017 applies an autocorrelation function for this purpose, as mentioned above. It was realised that the use of this autocorrelation function may also be extended to the present invention if the extracted part of the waveform is copied and appended to itself, so that two identical copies of the extracted part of the waveform may be used as the input for the autocorrelation function. Copying the extracted part of the waveform and analysing it in this manner ensures that the analysis conducted is still a beat-by-beat analysis. The results of the autocorrelation moreover purely relate to the heart beat under consideration, rather than to data relating to a longer period of time, such as to several heart beats. It is noted that the appending of one copy of the extracted waveform to another copy of the extracted waveform may generate a waveform that has a periodicity different from that of the originally recorded waveform. This is because preferred embodiments of the invention rely on a truncation or extension of the part of the waveform relating to a single beat, as discussed above. It is therefore not possible to determine a multi beat heart rate of the patient from this data and the multi beat heart rate of the patient may therefore be determined in a different manner, for example through ECG measurements or by performing the autocorrelation function disclosed in WO 97/00017 on a number of heart beats of the originally acquired waveform.

It is noted that a heart rate determined based pressure waveform data relating to a single beat only when extended or truncated in the manner described above may nevertheless provide useful information to medical practitioners. This is because such single beat heart rate data is prone to short term fluctuations. Such fluctuations may occur in reaction to short term changes in the conditions surrounding the heart and may therefore be indicative of such short term changes. A typical change influencing stroke volume are respiratory variations in thoracic pressure which reduce or increase the venous blood flow back to the heart and hence change the volume of blood available to be ejected by the ventricle during systole. As will be discussed later, such changes in thoracic pressure can influence the point in time at which the diastolic pressure corresponds to the pressure at the beginning of the systole. Determining a single beat heart rate may consequently provide a way of estimating or even quantifying short term influences, such as respiratory variations in thoracic pressure. Information on the heart rate determined from data relating to a single heart beat only may, for example, allow determination of respiration dependent variation in stroke volume/cardiac output. This information in turn may provide a useful insight into a patient's likely fluid responsiveness, as set out in more detail below.

The autocorrelation technique involves the subtraction of the mean of the compliance corrected waveform, a copying of the waveform created in this way and a shifting of the two copies of the waveform relative to each other. For each step of the shifting operation the values of the two copies of the waveform are multiplied with each other and the results of these multiplications are summed. Thus, for example for a shift of zero data points, the first data point of the first waveform is multiplied with the first data point of the second waveform, the second data point of the first waveform is multiplied with the second data point of the second waveform etc and the results of these multiplications are summed. For a shift of one data point the first data point of the first waveform is multiplied with the second data point of the second waveform, the second data point of the first waveform is multiplied with the third data point of the second waveform etc. and the results of these multiplications are again summed. The shift between the two copies of the waveform may be referred to as $\tau$. For each value of $\tau$ the mean is calculated by division of the summed value by the number of data points. Each mean is then a point on an auto-covariance/correlation plot.

The pulsatile changes within the waveform can then be evaluated by:

$$\text{pulsatility} = \sqrt{R(0)} + \sqrt{-R(\tau_{min})} \quad (2)$$

wherein $R(\tau)$ is the autocorrelation function, with $\tau_{min}$ indicating the value of $\tau$ at which the autocorrelation function is at a minimum. $R(0)$ is the maximum value (where $\tau$ is zero) of the autocorrelation function. The pulsatility corresponds to the relative stroke volume of the patient, based on which changes in the patient's cardiac output can be monitored. The absolute stroke volume can be determined by multiplying the pulsatility with the above described calibration factor cal.

Other ways of evaluating the pulsatility of the waveform can of course also be envisaged and ways of considering the pulsatile components of the waveform in the frequency domain following Fourier transformation are also known. Other ways of determining the root mean square value of the waveform following subtraction of its mean value may alternatively be used to determine the pulsatility of the arterial pressure waveform.

It will be appreciated that the pulsatile components of the arterial pressure waveform can alternatively be analysed without first applying the non-linear correction. The results of the analysis may later be made the subject of non-linear compliance correction in the manner described above with reference to equation (1). Alternatively, the results of such an analysis of the uncorrected arterial pressure waveform may directly be used as an indication of changes in the output of a patient's heart, although this may be less accurate.

Returning now to the manner in which a part of the arterial pressure waveform relating to a heart beat is extracted from the recorded pressure waveform, and considering the present invention in more general terms, it will be appreciated that when the systolic pressure decays to a value that is lower than the starting value or fails to decay to the starting value, this decay behaviour may simply be a manifestation of a baseline change in the arterial blood pressure data, for example due to a change in thoracic pressure. Correcting such changes has been recognised as being advantageous in its own right and according to another aspect of the present invention there is provided an apparatus for determining cardiac stroke volume comprising an input for receiving an arterial pressure waveform, means arranged to identify a baseline change in the arterial pressure waveform, means arranged to identify a part of the pressure waveform relating to a single heart beat, means arranged to correct the identified part to account for said baseline change and means arranged to calculate the pulsatility/stroke volume from the corrected part of the waveform.

It will be appreciated that a failure of the arterial blood pressure to return to the value it had at the beginning of a heart beat may be caused by the presence of an irregular heart beat. In this case the arterial blood pressure curve is extended until the pressure value present at the beginning of the heart beat is achieved, as discussed above. Put in other words, any increase in blood pressure caused by the additional or irregular heart beat is ignored for the purpose of assessing the stroke volume of the preceding beat. This has been recognised as being advantageous in its own right and according to another aspect of the present invention there is provided an apparatus for determining stroke volume comprising an input for receiving an arterial pressure waveform, the apparatus arranged to correct a part of the pressure waveform that relates to a single heart beat in a manner that removes an influence of an ectopic heart beat or of atrial fibrillation on the pressure waveform, the apparatus further comprising means arranged to calculate the stroke volume from the corrected waveform relating to the single heart beat.

The apparatus may be arranged to identify a trend of reducing data values in the last half, third, quarter or fifth of a part of the waveform relating to one heart beat and extrapolating the waveform by continuing the identified trend until a value is reached that substantially corresponds to the value of the starting point. Identifying the trend can comprise determining a gradient in the later part of the waveform and the trend may be continued by extending the waveform using the determined gradient. It will be appreciated that a trend can also be identified in a different manner, for example by fitting a mathematical function or curve to the later parts of the waveform. In this case the trend can be continued by extrapolating based on the fitted curve.

Once the stroke volume has been determined the cardiac output can be derived by multiplying stroke volume with the patient's heart rate, either the heart rate averaged over several beats or a single beat heart rate that may have been determined as discussed above.

Stroke volume values or cardiac output values may be determined over a period of time, i.e. for a number of heart beats. An indication may then be provided should a fluctuation in stroke volume, single beat heart rate or cardiac output over time exceed a predetermined value. It will be appreciated from the above discussion that thoracic pressure influences the start and end pressures of a heart beat's pressure waveform. Changes in thoracic pressure can also have an effect on the actual stroke volume and decrease stroke volume with increasing thoracic pressure and vice versa. Changes in stroke volume with thoracic pressure were noticed as being more pronounced in patient's with reduced blood volume in their circulatory system. Changes in stroke volume over a respiratory cycle may thus be used as an indication of the hemodynamic status of a patient and may be useful in deciding whether or not a patient should be given and/or will respond by increasing stroke volume and cardiac output to an increased amount of fluids. It is, for example envisaged that the apparatus may indicate whether or not the changes in stroke volume that are due to respiration or over a respiratory cycle are above a predetermined value of, for example, 10%. Should this be the case then the clinician can use the indication provided by the apparatus as one indication based on which he or she may decide to increase the amount of fluid given to the patient. Equally, should the changes in stroke volume be smaller than a predetermined value, then the clinician may take an indication provided by the apparatus to this effect as further information that may be useful in deciding whether or not the patient should be given a diuretic substance and/or whether or not fluid administration to the patient should be reduced. The predetermined value may be a fluid fluctuation value that is known to be associated with a clinically acceptable blood volume. Such a predetermined value may, for example, be based on empirical data.

Indications of the above nature may be provided by any output means, be that for example in a visual or audible form but may most conveniently be displayed on a display device. Displays on such display devices may output an indication of at least one of a current stroke volume, a current heart rate, a number of previous stroke volumes and a number of previous heart rates.

The cyclical changes in the stroke volume with the patient's respiration may also be used as the basis for a measurement of the patient's respiratory rate. This may be done by analysing the obtained pressure waveform so as to determine fluctuations in the average arterial pressure or in the calculated stroke volume over a period of time, say a few tens of seconds. This may be done using autocorrelation on a series of the determined stroke volumes or cardiac output values or by Fourier transformation of the series of stroke volumes or cardiac output values, for example.

The present invention is of course not only limited to the above described apparatus and further extends to corresponding methods. According to another aspect of the present invention there is therefore provided a method of determining cardiac stroke volume comprising receiving as an input an arterial pressure waveform, defining a start point for the purpose of determining stroke volume within the waveform at the beginning of a systolic arterial pressure increase, determining an end point for the purpose of determining stroke volume by performing at least one or both of identifying a part or point of the waveform that has substantially the same value as the starting point or extrapolating the waveform from the end of the diastole to a point where it has substantially the same value as at the beginning of the systole, and calculating the stroke volume from the whole of the now corrected single blood pressure cardiac cycle, including all the pressure values of the waveform or of the extrapolated waveform extending between the starting point and the determined end point.

According to another aspect of the present invention there is provided a method of determining stroke volume comprising receiving at an input an arterial pressure waveform, identifying a baseline change in the arterial pressure waveform, identifying a part of the pressure waveform relating to a heart beat, correcting the identified part to account for said baseline change and calculating the stroke volume from the corrected waveform.

According to another aspect of the present invention there is provided a method of determining stroke volume comprising receiving an arterial pressure waveform at an input, correcting a part of the pressure waveform that relates to a single heart beat in a manner that removes an influence of an ectopic heart beat or of atrial fibrillation on the pressure waveform and calculating the stroke volume from the corrected waveform.

According to another aspect of the present invention there is provided a method of monitoring a patient's fluid dynamics comprising monitoring the patient's cardiac output or stroke volume using any of the above described methods and determining whether or not a fluctuation in the stroke volume or cardiac output over a respiratory cycle exceeds a predetermined value, such as 10%. The method may further comprise increasing or reducing fluid input to the patient if the fluctuation is equal to or exceeds or is less than said predetermined value.

According to another aspect of the present invention there is provided a method of monitoring a patient's fluid dynamics comprising monitoring the patient's cardiac output or stroke volume using any of the above described methods and determining whether or not a fluctuation in the stroke volume or cardiac output over a respiratory cycle is less than a predetermined value. If the fluctuation is less than the predetermined value this may be taken as an indication that there is an excess of fluid in the patient's body and a diuretic substance may consequently be applied to the patient.

According to another aspect of the present invention there is also provided a method of monitoring a patient's respiration comprising determining a cardiac stroke volume of the patient over a period of time using any of the above described methods and determining a patient's respiratory rate based on cyclic changes, such as baseline changes, in the stroke volume.

Any of the above discussed method may further comprise the step of obtaining a pressure signal from a ventilator. The periodicity associated with a patient's respiration can be evaluated based on this pressure signal and the duration of one respiratory cycle can be determined. A fluctuation of the stroke volume over a respiratory period can then be determined based on the determined length of the respiratory cycle and on the stroke volume information. The beginnings of an inhalation or exhalation phase and the respective ends of the exhalation and inhalation phases can moreover be determined based on the pressure signal from the ventilator, for example by determining the points in the pressure signal where the gradient of the pressure signal changes from negative to positive (this point marks the beginning of the inhalation phase/the end of the exhalation phase) and by determining the points in the pressure signal where the gradient of the pressure signal changes from positive to negative (this point marks the end of the inhalation phase/the beginning of the exhalation phase).

DETAILED DESCRIPTION OF PREFERRED EMBODIMENTS

Figure 1A:
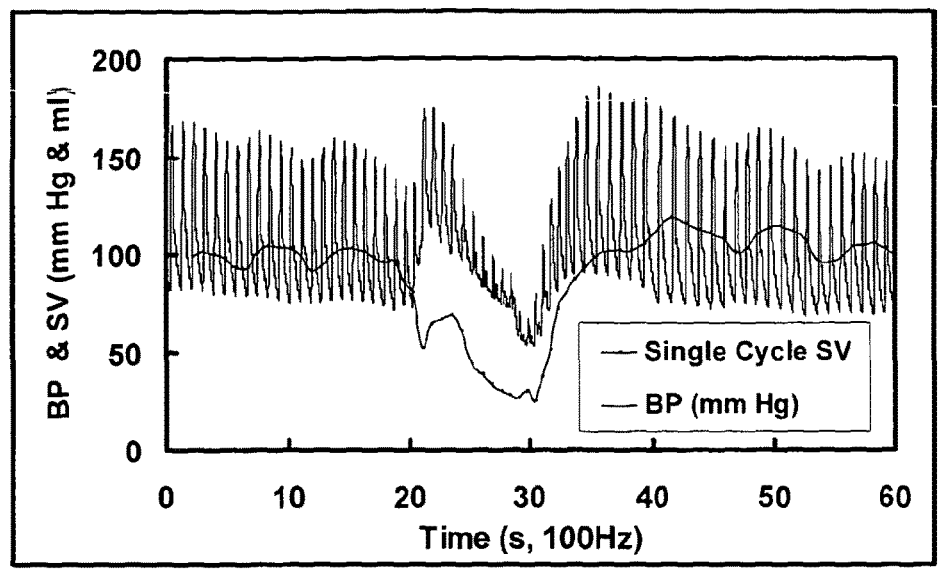
FIG. 1A shows the results of a measurement recording the changes in arterial blood pressure and stroke volume over time during a Valsalva manoeuvre according to an embodiment of the invention.
Figure 1:
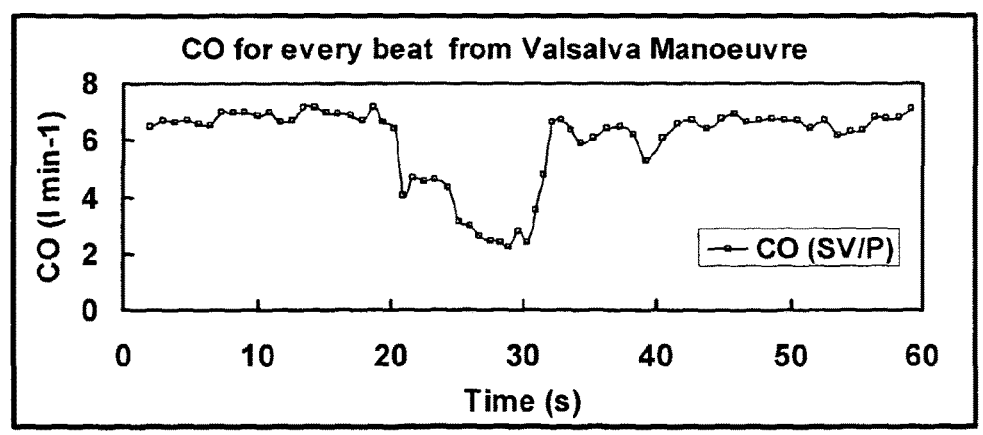
FIG. 1B shows the cardiac output calculated based on the stroke volumes shown in FIG. 1A.

FIG. 1A displays the variations in blood pressure BP in mmHg over time before, during and after a Valsalva manoeuvre. Also shown in FIG. 1A is the resulting stroke volume SV in nil over time. The more rapidly cyclically varying curve is the curve displaying blood pressure with the peaks in this curve indicating systolic blood pressure values. FIG. 1B shows the cardiac output for each heart beat determined from the stroke volume waveform shown in FIG. 1A by multiplying the stroke volume with the current heart rate.

As can be seen from FIG. 1A, up to about 18 s after the beginning of the measurement the maximum and minimum blood pressure vary cyclically. This variation is due to the subject's respiration and brings about a consequential variation in stroke volume. After about 22 s a marked increase in both maximum and minimum blood pressure values as well as in stroke volume can be observed. This increase is due to the initial pressure increase in the subject's thorax, which causes an initial expulsion of blood from the arterial part of the subject's thorax into more peripheral parts of the subject's arterial system. This phase ends at about 23 s after the beginning of data recording and is followed by a steep decrease in maximum and minimum blood pressure values caused by the constraint which increased thoracic pressure places on the heart's ability to fill with and consequently to eject blood. The increased thoracic pressure not only affects the heart's ability to pump blood, it also compresses the veins in the thorax, thereby reducing the volume of blood upstream of the heart that is available for filling the heart during diastole. After the end of the Valsalva manoeuvre at about 30 s, that is after the artificial increase in thoracic pressure has been removed, the minimum and maximum blood pressure values alongside the stroke volume increase to a normal level.

Figure 2:
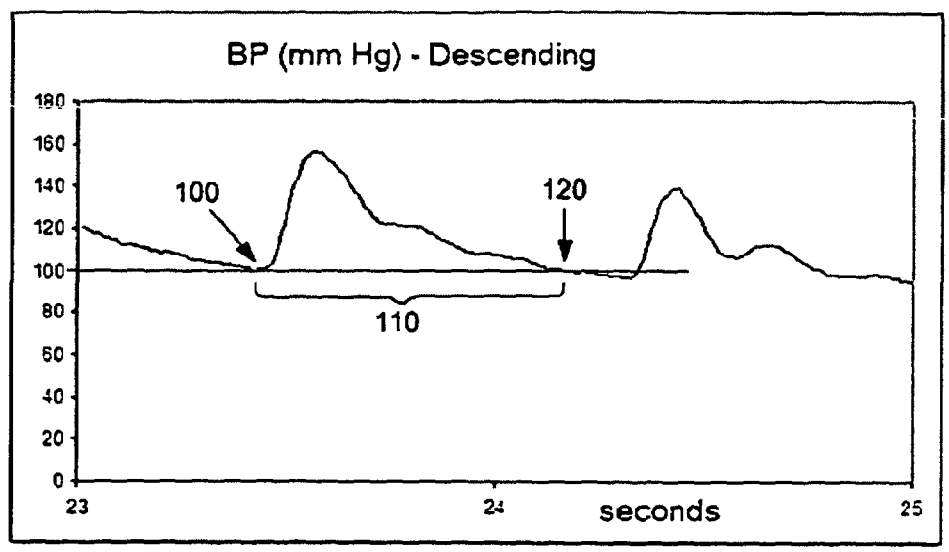
FIGS. 2A and 2B show a part of the arterial blood pressure waveform of FIG. 1A and illustrate a manner in which a preferred embodiment processes the illustrated waveform data.
Figure 2:
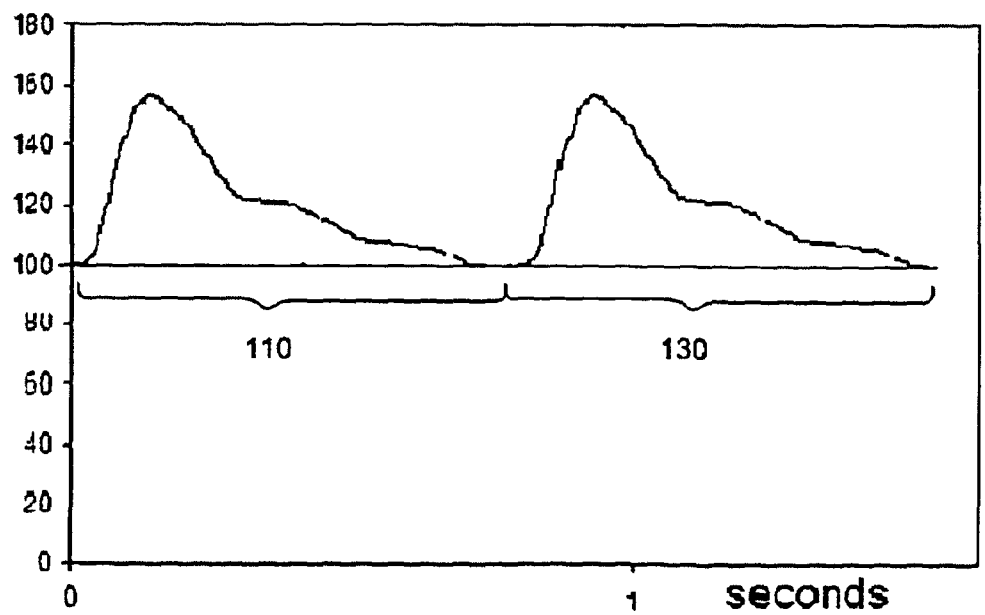
Figure 3:
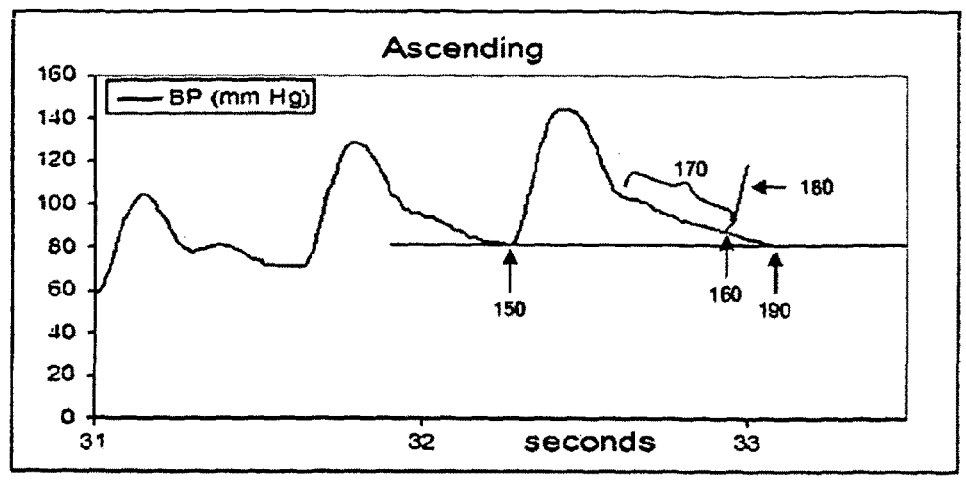
FIGS. 3A and 3B show another part of the arterial blood pressure waveform of FIG. 1A and illustrate a manner in which a preferred embodiment processes the illustrated waveform data.

It will be appreciated from FIG. 1A that during the Valsalva manoeuvre the minimum blood pressure at the end of a heart beat either does not return to the starting value (as is the case in FIG. 1A between about 22 s and 24 s and between about 30 s and 35 s) or returns to a value that is below the starting value (as is the case in FIG. 1A between about 24 s and 30 s). As discussed above, in situations of this nature it is likely that a stroke volume calculated from the arterial blood pressure waveform is under-or over-estimated respectively. FIGS. 2A and 3A illustrate a situation in which the diastolic blood pressure at the end of a heart beat decreases below the diastolic blood pressure at the beginning of the heart beat and a situation in which the diastolic blood pressure at the end of a heart beat does not decrease to the diastolic blood pressure at the beginning of the heart beat respectively.

FIG. 2A in particular shows an extract of the part of the blood pressure waveform of FIG. 1A extending between 23 s and 25 s after the beginning of data recording, that is during the phase of the Valsalva manoeuvre in which the blood pressure values have started to decrease. The arterial diastolic pressure at the beginning of the heart beat is about 100 mm Hg at a starting point labelled 100 at the beginning of the heart beat. The arterial blood pressure at the end of the heart beat, however, decreases below this starting value, as can be seen from the horizontal line superimposed over the pressure waveform. It was found that, if this decrease were taken into account in calculating stroke volume, the derived stroke volume would not be correct.

FIG. 2B shows the manner in which the present invention in one embodiment overcomes this problem. As can be seen from FIG. 2B, the part 110 of the waveform of FIG. 2A that is above the arterial blood pressure value at the starting point 100, that is the part extending from the starting point 100 to the end point 120 at which the waveform intersects the superimposed horizontal line, has been extracted. A copy 130 of the extracted part 120 of the waveform has then been appended to the extracted part of the waveform. This combination of waveforms thus provides a data sequence that is suitable as input for the above described autocorrelation method of determining pulsatility, stroke volume and cardiac output.

FIG. 3A shows the part of the waveform of FIG. 1A between 31 s and 33.5 s after the start of data recording during the part of the Valsalva manoeuvre following the reduction of thoracic pressure. As can be seen from FIG. 3A, the arterial pressure at a starting point 150 at the beginning of a heart beat is less than the arterial pressure at a point 160 at the beginning of the next heart beat, as again indicated by a horizontal line superimposed over the pressure waveform. As discussed above, this can again lead to a situation where the stroke volume is determined from the arterial pressure waveform in an incorrect fashion.

FIG. 3A also indicates the manner in which the embodiment addresses this change in diastolic pressure to ensure that the correct stroke volume can nevertheless be calculated. As can in particular be seen from FIG. 3A, the later part 170 of the pressure waveform has been extended until it reaches the pressure value corresponding to the pressure value at the starting point 150. Although the pressure increase 180 that comes with the beginning of the following heart beat is still shown in FIG. 3A, this pressure increase 180 is only presented in this figure to show clearly how the waveform relating to the heart beat has been extended. The data that are part of the pressure increase 180 are of course not taken into account when determining stroke volume. The relevant part of the later section of the waveform shown in FIG. 3A is thus the descending part extending to the end point 190.

Figure 3B:
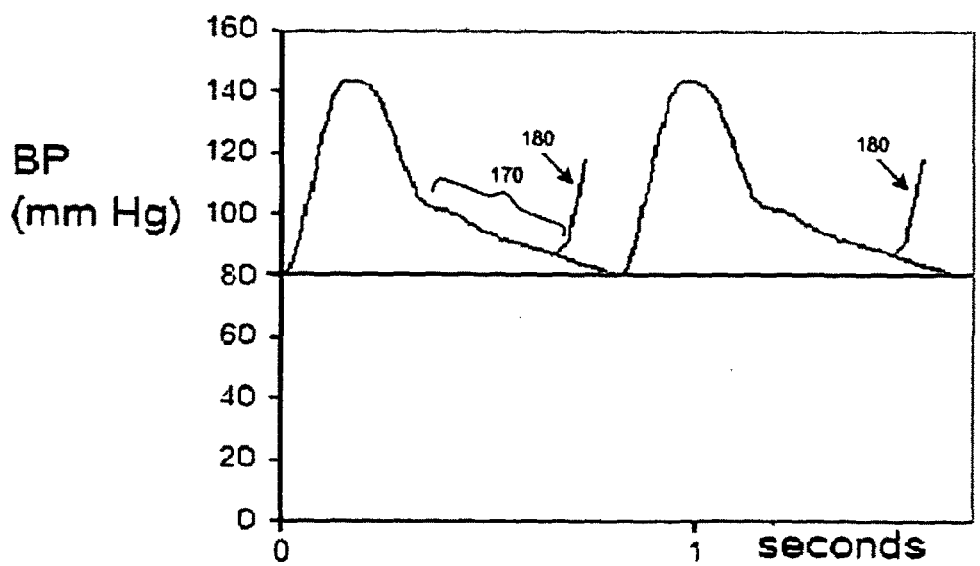

FIG. 3B shows the concatenation of the extended/extrapolated and extracted part of the waveform of FIG. 3A extending between the starting point 150 and the end point 190 shown in FIG. 3A with a copy of the same waveform. The pressure increase 180 that forms part of the beginning of the following beat is again shown in FIG. 3B to clearly illustrate the manner in which the waveform has been extended. These pressure increases 180 are not data that are included in subsequent data analysis. The waveform shown in FIG. 3B again forms a suitable input for the above discussed autocorrelation method for determining pulsatility, stroke volume and cardiac output.

Figure 4:
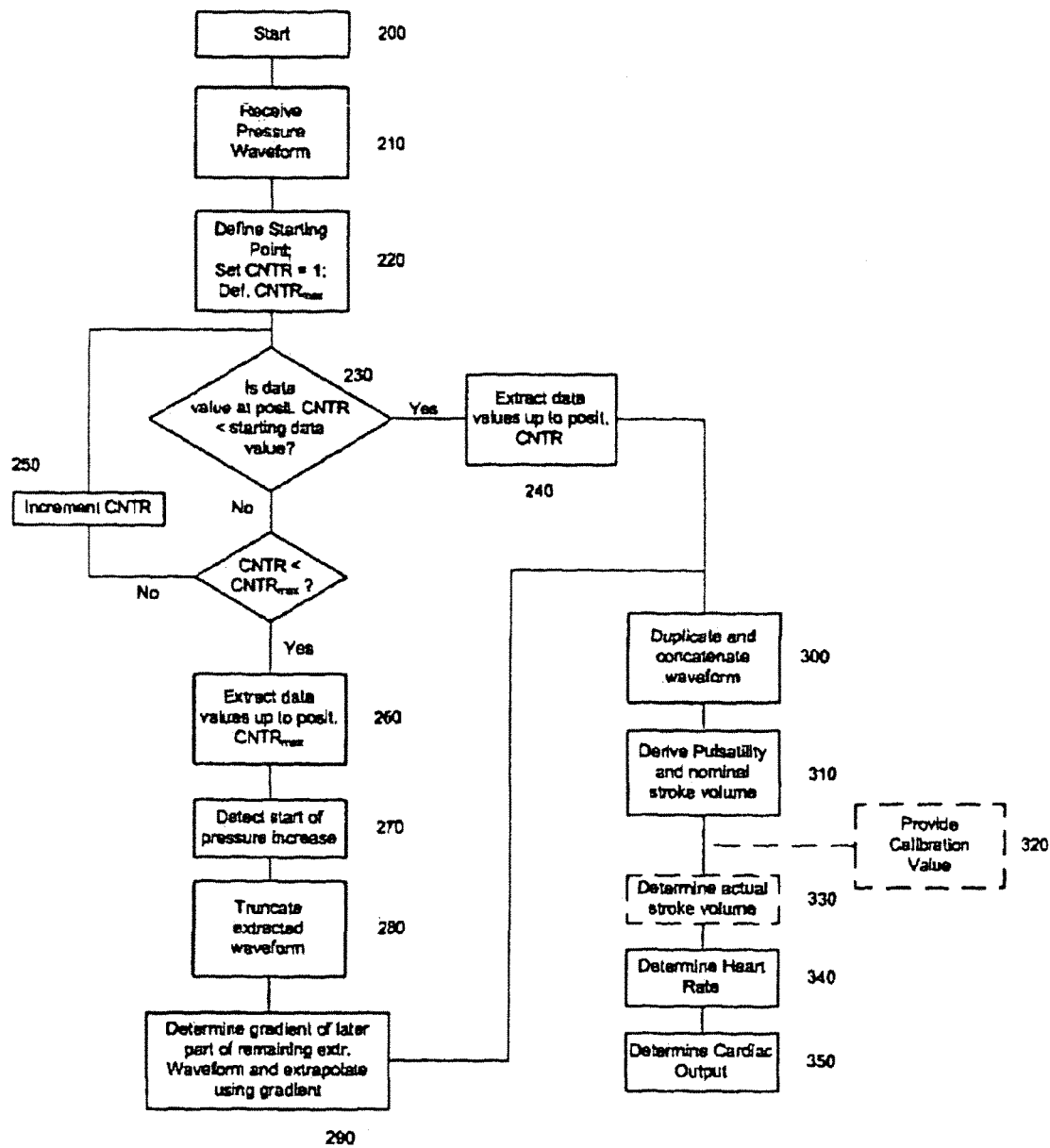
FIG. 4 shows a flow chart of a preferred embodiment.

FIG. 4 shows a flow chart of a method according to an embodiment. The method is started at step 200 and pressure waveform data is received at step 210. At step 220 a starting point at the beginning of a systolic arterial pressure increase, such as starting point 100 or 150 is defined and the arterial pressure value at that point is noted, for example by storing it in a register. A counter CNTR is at the same time set to a starting value of one and a maximum counter value $CNTR_{max}$ is defined. The maximum counter value $CNTR_{max}$ is for interrupting a loop in which the data following the starting point are analysed. The value of $CNTR_{max}$ depends on the likely expected heart rate as well as the sampling frequency used for sampling the patient's arterial pressure and should sensibly be set so that the loop (described in more detail below) covers data expected to relate to a full heart beat plus some further data points to provide a safety margin. The next data point is analysed in step 230. The number of data points by which this 'current' data point is spaced apart from the start point corresponds to the value of the counter CNTR. If the comparison indicates that the data value is smaller than the starting value then the method has identified the end point (namely the data point at the position indicted by the counter CNTR) proceeds to step 240. In step 240 the part of the waveform, extending between the starting point and the newly identified end point is extracted. If the comparison indicates that the data value is larger than the data value at the starting point, the counter value is compared to the maximum counter value $CNTR_{max}$.

If CNTR is smaller than $CNTR_{max}$, then the process returns to step 230 via step 250, in which the counter CNTR is incremented by one. Otherwise the process proceeds to step 260, in which a part of the pressure waveform is extracted. This part extends from the starting point to a point $CNTR_{max}$ data points away from the starting point. The second half of the waveform extracted in this way is analysed in step 270 and a point at which the arterial pressure starts to increase, such as point 160 shown in FIG. 3A, is detected. In step 280 the extracted data set is truncated to exclude the data values from the detected point to the end of the extracted data set. In step 290 the averaged gradient of the later parts of the remaining waveform is determined and the gradient determined in this way is used for extrapolating the waveform until the extrapolated pressure value is equal to or lower than the arterial pressure at the beginning of the waveform.

The method proceeds to step 300 from both step 240 and step 290. At step 300 a waveform will therefore have either been extracted from the original pressure waveform, if the method had progressed to step 300 from step 240, or, if the method has progressed to step 300 from step 290, extracted and extrapolated, as described in more detail above. The resulting waveform is duplicated in step 300 and one copy appended to the other copy of this waveform. In step 310 autocorrelation is used in the manner described in more detail above to derive the pulsatility of the waveform based on equation (2) to calculate the nominal stroke volume. Optionally a calibration value may be received or determined in step 320 and used to calculate an actual stroke volume from the nominal stroke volume in step 330. The heart rate is determined in step 340, for example using autocorrelation based on the originally recorded waveform in the manner described in WO 97/00017 or based on the waveform relating to a single beat. The heart rate is multiplied with the nominal or the actual stroke volume in step 350 to provide a current nominal or actual cardiac output value.

The person skilled in the art will understand that the above described method is only one of several possible methods of putting the invention into practice. Modifications to the above described method are therefore envisaged. It is, for example, envisaged that step 260 may be omitted and that the process directly proceeds to step 270 so that the extrapolated data simply replace the original unwanted data. It is further envisaged that the counter CNTR may be incremented by more than one in step 250. This facilitates a more rapid detection of a point at which the diastolic pressure decreases to below the diastolic at the starting point of the current arterial pressure waveform. Once a point at which the arterial pressure is below the starting arterial pressure has been detected the data points between the point currently under consideration and the previously considered data point can be compared to the arterial pressure at the start of the waveform one-by-one to identify the first point of the waveform at which the arterial pressure has decreased below the starting arterial pressure.

Figure 5:
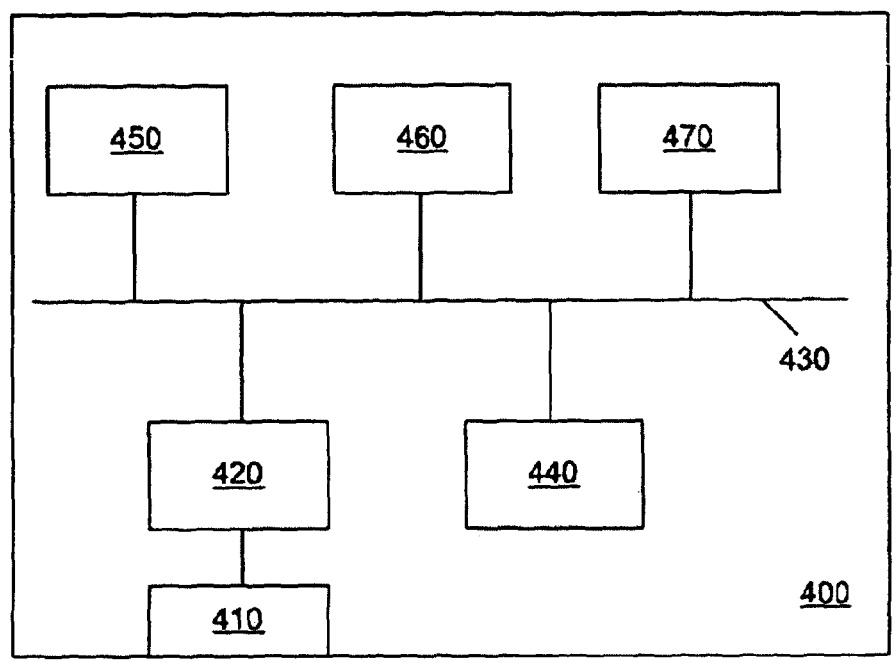
FIG. 5 shows an overview of a hemodynamic monitor in which an embodiment of the present invention can be implemented.

FIG. 5 shows an overview of a hemodynamic monitor 400 in which an embodiment of the present invention can be implemented. The hemodynamic monitor comprises an input port 410 to which a device providing an analogue pressure waveform can be connected and through which the analogue pressure waveform can be input into the hemodynamic monitor. An analogue to digital converter 420 is provided for converting any analogue pressure waveform received through the input port 410 into a digital signal. The digital signal can be placed on the bus 430 for further processing, as discussed below. The hemodynamic monitor 400 further comprises a microprocessor 440, a RAM 450, which may act as buffer, permanent storage means provided in the form of a hard drive 460 and some input/output means 470. Examples of such input/output means are monitors, printers and keyboards etc.

Figure 6:
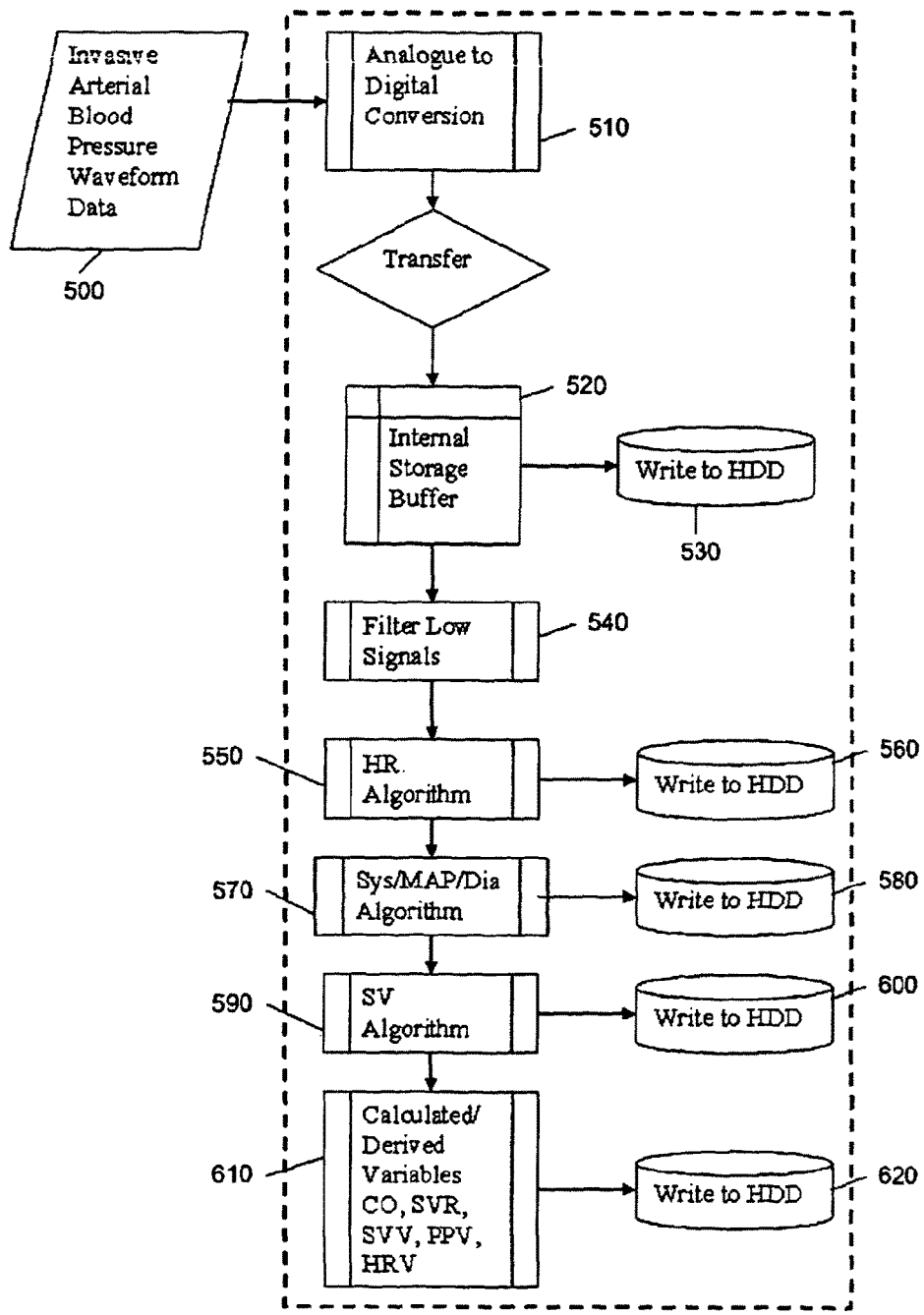
FIG. 6 illustrates data processing steps performed in the hemodynamic monitor.

FIG. 6 illustrates data processing steps performed in the hemodynamic monitor of a preferred embodiment. In step 500 an analogue pressure waveform is received from an external device. The analogue digital converter 420 converts the analogue pressure waveform into a digital signal in step 510 and transfers it to the internal buffer/RAM 450 in step 520. Optionally the digital pressure waveform is stored on the hard drive 470 in step 530. The digital signal is then filtered in step 540 by the microprocessor 440 to suppress noise. The filtering in step 540 may use a low pass filter. The microprocessor determines the single beat or multi-beat heart rate HR associated with the pressure waveform in step 550. Optionally the determined heart rate is stored on the hard drive 460 in step 560.

In step 570 the microprocessor 440 determines the maximum/systolic blood pressure value (indicated as "Sys" in step 570 of FIG. 6), the minimum/diastolic blood pressure value (indicated as "Dia" in step 570 of FIG. 6) and the mean arterial pressure value (indicated as "MAP" in step 570 of FIG. 6) from the arterial pressure waveform. The mean arterial pressure value may be derived based on data relating to a single heart beat, truncated or extended as discussed above, or from data relating to several heart beats. Optionally the determined pressure values are stored on the hard drive 460 in step 580.

In step 590 the microprocessor determines the stroke volume SV for a single heart beat using the above described algorithm and optionally the so determined stroke volume value is stored on the hard drive 460 in step 600. In step 610 the microprocessor calculates the cardiac output CO as the product of heart rate HR (be that a multi beat heart rate or a single beat heart rate) and stroke volume SV, SVR as the quotient of mean arterial pressure MAP and cardiac output CO, stroke volume variation SVV % as the change (expressed as a percentage) in stroke volume over a 10 s time window ((stroke volume max—stroke volume min)/mean stroke volume), pulse pressure variation PPV % as the change (expressed as a percentage) in the difference between the pulse pressure (systolic—diastolic pressure) max—pulse pressure min over a time window, such as a 10 s time window, the variation in the heart rate (HRV) as the quotient of the standard deviation of the heart rate from the mean heart rate over a time window, such as a 10 s time window, and the mean heart rate over this time window. HRV can be determined either based on single beat heart rate information or on multi-beat heart rate information. It will be appreciated that, over a relatively short time period, such as the above mentioned time period of 10 s, HRV based on heart rate values determined based on information relating to multiple heart beats may vary less widely than HRV values determined based on single beat heart rate data. Optionally the so derived values are stored on the hard drive 460 in step 620. Some or all of the measured and/or the derived values are then displayed on a display.

It will be appreciated that the above description of the present invention is made by way of example only to illustrate the present invention. The person skilled in the art will appreciate that the present invention is not limited by the examples provided above. It will, for example, be appreciated that the pressure waveforms shown in FIGS. 2B and 3B do not necessarily have to be analysed using the above described autocorrelation method of analysing pressure waveforms and that other suitable ways of analysis arterial pressure data may instead be used to determine stroke volume and/or cardiac output based on the extracted data. It will moreover be appreciated that other modifications to the above described preferred embodiment may be made without departing from the scope of the claims. It can, for example, be envisaged that the architecture of the hemodynamic monitor differs from the example architecture shown herein. The pressure waveform may, for example, be received in a digital form, thereby eliminating the need for the analogue to digital converter. Alternatively the hemodynamic monitor itself may comprise means for measuring the arterial blood pressure signal upon which the above described analysis is based, rather than having to rely on an external arterial pressure measuring device.

The invention claimed is:

1. An apparatus for determining stroke volume comprising:
    an input for receiving an arterial pressure waveform;
    means arranged to define a start point within the arterial pressure waveform at a beginning of a systolic arterial pressure increase due to a ventricular contraction phase of a heart beat;
    means arranged to determine an end point of the heart beat for the purpose of calculating stroke volume by
        determining whether there is a part or point of the arterial pressure waveform that has substantially the same arterial pressure value as said starting point,
        responsive to said arterial pressure value at said starting point being regained, setting the end point to be the part or point of the arterial pressure waveform that has substantially the same arterial pressure value as said starting point, and
        responsive to said arterial pressure value at said starting point not being regained, extrapolating the end point of the heart beat to a point where the arterial pressure waveform has substantially the same arterial pressure value as said starting point to define the end point;
    means arranged to calculate a stroke volume from a part of the arterial pressure waveform or of the extrapolated arterial pressure waveform between the start point and the end point; and
    an output means and configured to output, via the output means, an indication of at least one of a current stroke volume, a current heart rate, a number of previous stroke volumes and a number of previous heart rates.

2. The apparatus according to claim 1 further comprising:
    means arranged to identify a baseline change in the arterial pressure waveform; and
    means arranged to correct the part of the arterial pressure waveform or of the extrapolated arterial pressure waveform between the start point and the end point to account for said baseline change;

wherein the stroke volume is calculated from the corrected part of the arterial pressure waveform or of the extrapolated arterial pressure waveform.

3. The apparatus of claim 1, the apparatus configured to correct part of the arterial pressure waveform or of the extrapolated arterial pressure waveform between the start point and the end point for an influence of an ectopic heart beat or of atrial fibrillation or of respiratory changes on the pressure waveform, wherein the stroke volume is calculated from the corrected part of the arterial pressure waveform or of the extrapolated arterial pressure waveform.

4. An apparatus according to claim 1, further configured to identify a trend in the last half, third, quarter or fifth of a part of the arterial pressure waveform relating to one heart beat and extrapolating the arterial pressure waveform by continuing the identified trend until a value substantially corresponding to the value of the start point is reached.

5. An apparatus according to claim 4, wherein identifying said trend comprises determining a gradient in the said part of the arterial pressure waveform and wherein continuing the trend comprises extending the arterial pressure waveform using the determined gradient.

6. An apparatus according to claim 1, further configured to apply a non-linear correction to the arterial pressure waveform.

7. An apparatus according to claim 1, further configured to calculate the stroke volume by determining the pulsatility of the part of the arterial pressure waveform relating to a heart beat between the start point and the end point.

8. An apparatus according to claim 7, further configured to determine an absolute stroke volume by multiplying the pulsatility with a calibration factor specific to a patient.

9. An apparatus according to claim 1, configured to determine cardiac output by multiplying stroke volume with a heart rate.

10. An apparatus according to claim 1, configured to store the stroke volumes or cardiac outputs for a number of heart beats and to provide an indication should a fluctuation in the stroke volume or the cardiac output over time exceed a predetermined value.

11. An apparatus according to claim 1, further configured to determine a heart rate based on the received arterial pressure waveform by performing autocorrelation on the arterial pressure waveform over a number of consecutive beats.

12. An apparatus for monitoring patient respiration comprising an apparatus according to claim 1, the apparatus configured to determine a respiratory rate based on cyclic changes in the stroke volume or cardiac output.

* * * * *